United States Patent [19]
Williams et al.

[11] Patent Number: 5,453,698
[45] Date of Patent: Sep. 26, 1995

[54] METHOD AND SYSTEM FOR TESTING AN IMPLANTABLE DEFIBRILLATOR OUTPUT STAGE AND HIGH VOLTAGE LEAD INTEGRITY

[75] Inventors: Michael O. Williams; Stephen T. Archer, both of Sunnyvale, Calif.

[73] Assignee: Ventirtex, Inc., Sunnyvale, Calif.

[21] Appl. No.: 314,025

[22] Filed: Sep. 28, 1994

[51] Int. Cl.⁶ .............................. G01R 27/26; A61N 1/39
[52] U.S. Cl. ................. 324/678; 324/537; 607/5; 607/27
[58] Field of Search ......................... 324/522, 537, 324/539, 555, 678; 607/5, 7, 27

[56] References Cited

U.S. PATENT DOCUMENTS

| | | | |
|---|---|---|---|
| 4,164,946 | 8/1979 | Langer | 128/419 |
| 4,233,659 | 11/1980 | Pirkle | 607/5 X |
| 5,111,816 | 5/1992 | Pless et al. | 128/419 |
| 5,159,276 | 10/1992 | Reddy | 324/678 |
| 5,201,865 | 4/1993 | Kuehn | 128/419 |
| 5,224,475 | 7/1993 | Berg et al. | 128/419 |
| 5,237,991 | 8/1993 | Baker, Jr. et al. | 607/27 |

*Primary Examiner*—Kenneth A. Wieder
*Assistant Examiner*—Glenn W. Brown
*Attorney, Agent, or Firm*—Steven M. Mitchell; Mark J. Meltzer

[57] ABSTRACT

A method and system for testing the integrity of a high voltage output stage and high voltage leads of an implantable cardioverter/defibrillator. The method and system comprises charging one or more high voltage capacitors associated with the high voltage output stage to a predetermined relatively low voltage on the order of 10–20 volts, discharging the high voltage capacitors synchronous with a sensed cardiac event for a predetermined time period, measuring a residual voltage on the high voltage capacitors, and then comparing the residual voltage to a reference voltage to assess the integrity of the output stage and high voltage leads.

8 Claims, 3 Drawing Sheets

5,453,698

METHOD AND SYSTEM FOR TESTING AN IMPLANTABLE DEFIBRILLATOR OUTPUT STAGE AND HIGH VOLTAGE LEAD INTEGRITY

FIELD OF THE INVENTION

This invention relates generally to implantable defibrillators and more particularly to implantable defibrillator test circuits and methods.

BACKGROUND OF THE INVENTION

The function of implantable Cardioverter/Defibrillators (ICDs) are now well known in the art. In general, ICDs apply electric pulses or shocks to the heart of a patient to terminate an abnormally rapid heart rate or tachyarrhythmia. Ventricular tachyarrhythmias, including tachycardia and fibrillation, typically involve premature or uncoordinated contraction of the ventricles of the heart which prevents the normal functioning and pumping of the heart. An implanted ICD may also include a pacemaker, to supply the heart with regular or intermittent pacing pulses in order to complement or induce regular heart rhythms.

Once such a device is implanted, the patient nonetheless does not become immune to cardiac difficulties. For one reason or other, despite the proper functioning of the ICD, circumstances may arise which require the use of an external defibrillator. The voltages applied during defibrillation, whether by an implanted device or an external device are very high. An example of a typical voltage level employed by an implanted defibrillator during defibrillation is 750 volts. For defibrillation by an external device, voltages of several thousand volts may be applied. When such a high voltage pulse is applied to the chest of a patient from an external device, and the patient has an ICD, substantial damage may result to the ICD. Accordingly, it is considered prudent to test the ICD following an external defibrillation to determine if replacement may be necessary. There also may be other reasons to test the high voltage (HV) output stage and defibrillation lead integrity such as a suspected lead break.

Many patents have been granted in the field of ICDs. For example, U.S. Pat. No. 5,111,816 has been issued to Benjamin Pless, John G. Ryan, and James M. Culp on a combined defibrillator/pacemaker. The patent shows a system which is able to detect defibrillation lead breaks without delivering a defibrillation pulse to the patient. Pseudounipolar pacing is performed from the pacing capacitors using the high voltage defibrillation leads as the ground return. The lead impedance can be estimated by measuring the initial and final voltages on the pacing capacitors. U.S. Pat. No. 4,164,949 has been granted to Alois A. Langer on the subject of fault detection in a permanently implanted cardioverter or defibrillator. The circuitry of the Langer patent includes built-in interrogation and testing and complex fibrillation detection circuitry used to monitor an ECG signal and to issue a fibrillation detection signal when predetermined characteristics are detected. A characteristic output signal is produced when the fibrillation detector circuit is functioning properly.

Another recent patent, U.S. Pat. No. 5,224,475 was granted to Berg, et al. in 1993 on a method and apparatus for termination of ventricular tachycardia and ventricular fibrillation. According to this patent, an implantable defibrillator is provided with a plurality of defibrillation electrodes which may be reconfigured to define a plurality of defibrillation pathways. The device measures impedance along selected defibrillation pathways and monitors the success or failure of the pulse to accomplish defibrillation or cardioversion. The impedance paths are measured while electric current is applied to the heart of a patient. The teachings of this patent accordingly help optimize the correct positioning of electrodes in the body of a patient to ensure effective defibrillation can be accomplished. The impedance testing performed helps in the optimization process.

However, the patents indicated above are not specifically directed toward determination of the integrity of the output stage and the high voltage leads in the defibrillation circuitry. These patents show approaches in dealing with detection of lead breakage. They disclose complex arrangements to optimize the placement of defibrillation electrodes.

U.S. Pat. application Ser. No. 08/172,510 filed on Dec. 22, 1993 entitled "Implantable Defibrillator Output Stage Test Circuitry and Method" and assigned to the assignee of this present application addresses some of these problems. The method and arrangement according to this patent application permit the checking of the condition of key high voltage output switches of a defibrillator, without application of shocks to the heart of a patient. The defibrillation output stage circuitry, according to one embodiment, includes a resistor connected between internal nodes connected to first and second switches respectively connected to a high voltage capacitive source and ground. The circuitry further includes a second resistor which provides an alternate path to ground which shunts the first resistor and the second switch to ground. By discharging the capacitive voltage source over given time periods, different voltage levels on the voltage source after expiration of the given time periods are indicative of different switch conditions, permitting convenient diagnosis of failed high voltage delivery switches, whether the switches are fused closed or simply fail to open or close at the appropriate times.

Although this invention works effectively for its intended purpose, it does not provide an indication of the integrity of the high voltage defibrillation leads. That is, it does not provide an accurate indication of whether the high voltage leads of the defibrillator are capable of functioning on an ongoing basis without failure. The high voltage lead integrity is a critical factor when delivering the defibrillation therapy to the heart. Accordingly, systems that can determine the high voltage lead integrity along with the integrity of the output stage are very important.

In accordance with the invention, it is an object to ascertain the integrity of selected ICD components to determine whether they are operating properly.

It is an object to test the high voltage lead integrity of the ICD.

It is further an object of the invention herein to detect the condition of ICD circuitry without additional circuitry.

It is further an object of the invention herein to detect the condition of ICD circuitry with the use of conventional ICD circuitry.

These and other advantages of the present invention will become apparent upon reading the following detailed descriptions and studying the various figures of the drawings.

SUMMARY OF THE INVENTION

A method and system for testing the integrity of a high voltage (HV) output stage and high voltage leads of an implantable cardioverter/defibrillator (ICD). The method and system comprise charging one or more high voltage capacitors within the high voltage output stage to a predetermined relatively low voltage, discharging the high voltage capacitor(s) synchronous with a sensed cardiac event for a predetermined time period, measuring a residual voltage on the high voltage capacitor(s), and then comparing the residual voltage to a reference voltage to assess the integrity of the output stage and high voltage leads.

Accordingly, through the use of a low voltage pulse (approximately 10–20 volts) through the HV output stage and the subsequent measurement of the residual voltage (VF), the HV output stage and high voltage lead integrity of an ICD system can be readily determined. This testing can take place through minimal modification to the hardware and software of the conventional ICD system.

DETAILED DESCRIPTION

Figure 1:
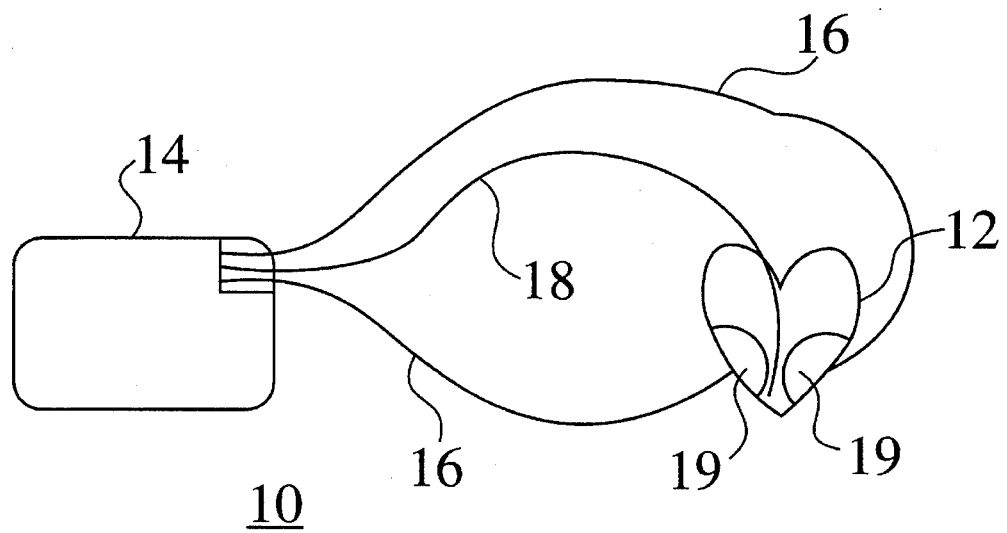
FIG. 1 is a simplified block diagram of an ICD system.

FIG. 1 is a simplified block diagram of the relevant portions of a conventional implantable cardioverter defibrillator (ICD) system 10. In such a system, pacing pulses are provided to the heart 12 and sense signals are received from the heart by ICD circuitry 14 via pace/sense lead 18. These pacing pulses are typically provided to the heart 12 from a pacing circuit within the ICD. High voltage cardioversion and defibrillation pulses are provided to the heart 12 in response to a detected tachyarrhythmia from a high voltage output stage in ICD circuitry 14 via high voltage leads 16.

The two high voltage leads 16 provide the high voltage (50–750 V) pulses to electrodes 19 to stimulate the heart 12 responsive to the detection of a tachyarrhythmia. In this embodiment, two high voltage leads 16 with patch electrodes 19 are shown for illustrative purposes only and one of ordinary skill in the art will readily recognize that there are numerous possible high voltage lead configurations including transvenous leads which could be used, and their use would be within the spirit and scope of the present invention.

The present invention takes advantage of the existing ICD system 10 to provide a method and apparatus for detecting the integrity of the high voltage leads 16 as well as the integrity of the HV output stage of the ICD circuitry 14.

Figure 2:
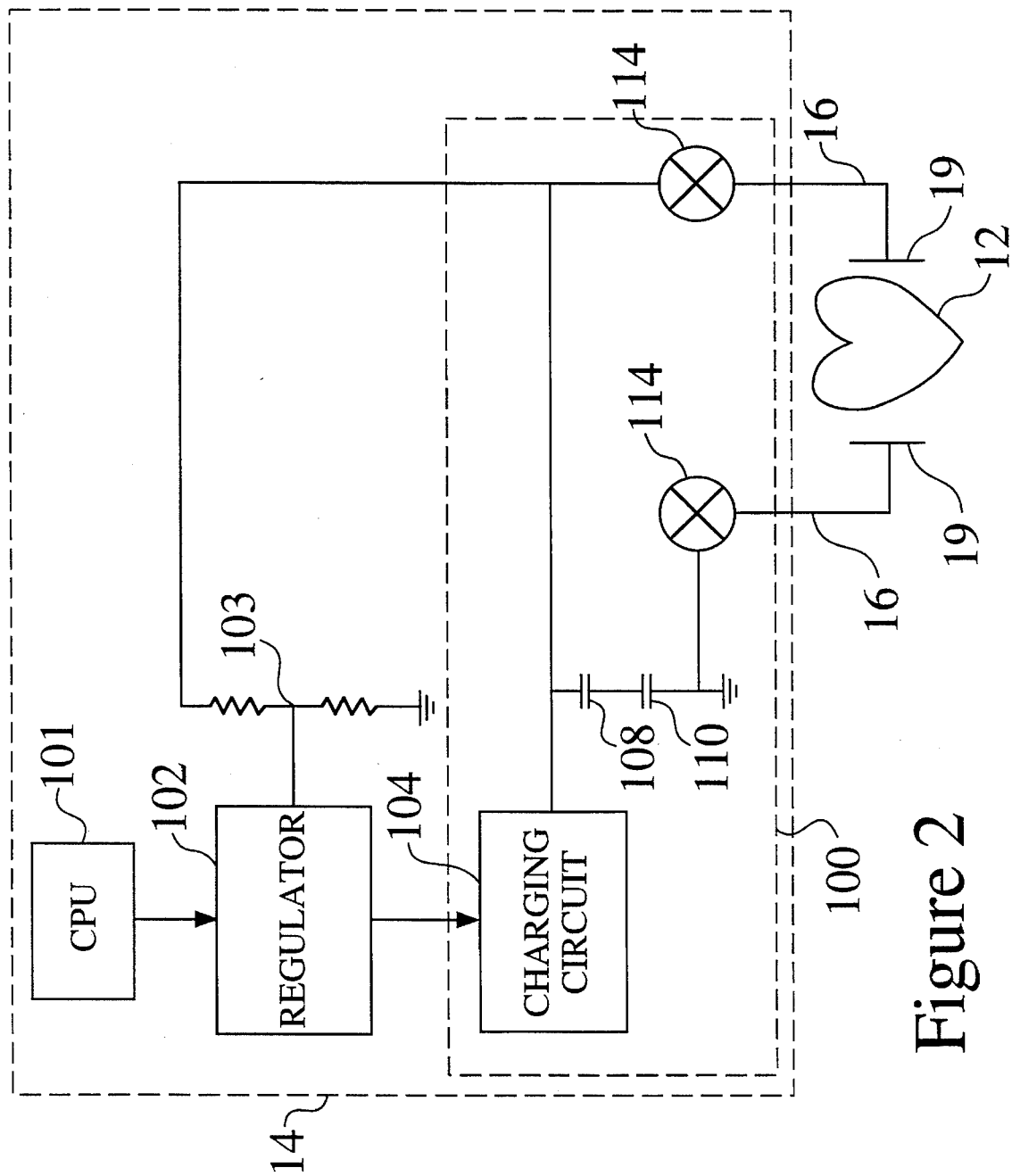
FIG. 2 is a block diagram of a high voltage output stage utilized in the ICD system in accordance with the present invention.

To more specifically describe the advantage of the present invention refer now to FIG. 2, which shows a schematic representation of the HV output stage 100 of a defibrillation system 10 coupled to high voltage leads 16 in accordance with the present invention.

In this embodiment, a regulator 102 under control of a microprocessor 101 is coupled to a charging circuit 104. In normal operation, the charging circuit 104 in turn charges the high voltage capacitors 108, 110 responsive to the detection of a rapid heart rate. Two HV capacitors are shown connected in series but the invention could be used with a single capacitor or a stack of three or more capacitors. The regulator 102, under control of microprocessor 101, typically provides a signal to charging circuit 104 indicating that delivery of a high voltage pulse to the heart 12 is to take place. The charging circuit 104 charges the capacitors 108 and 110 16 a predetermined voltage. Switches 114 are then opened for a predetermined time to discharge the high voltage (50 –750 V) through the high voltage leads 16 and electrodes 19 to cardiovert or defibrillate the heart 12. The above describes the normal operation of the HV output stage 100 and high voltage leads 16 for delivery of a monophasic HV pulse. Alternatively, some ICDs include an "H" bridge circuit for delivering a biphasic waveform pulse as described in U.S. Pat. No. 5,111,816 to Pless et al. discussed above.

Applicants have discovered that by detecting a change in the residual voltage for a low voltage pulse delivered from the high voltage capacitors 108, 110 of the HV output stage 100, it is possible to assess the integrity of the HV output stage 100 and of the high voltage leads 16 of the ICD system. In essence, by providing a low voltage pulse through the HV output stage 100 and the high voltage leads 16 which is of much less magnitude (on the order of 10–20 volts) than the normal high voltage pulse, a determination can be readily made as to the integrity of the high voltage leads 16 and HV output stage 100 without delivering an unnecessary high voltage shock to the patient. The residual voltage will be a function of the impedance of the HV output stage and the high voltage leads. A high impedance, i.e. high residual voltage, is indicative of lead break or other similar problem with the system. A very low impedance, i.e. low residual voltage, is indicative of a possible short somewhere in the system.

To more specifically describe the advantages of the present invention, please refer now to the following background information. As is well understood, the HV output stage 100 during operation can be represented as a capacitance (capacitors 108 and 110) which is in turn discharged through a resistance (high voltage leads 16 and the resistance of the body, essentially the cardiac tissue and blood, of the individual).

It is understood that the residual voltage ($V_F$) Of a truncated exponential pulse can be determined by providing a voltage through the HV output stage 100. If the value of $V_F$ changes significantly from measurement to measurement, that indicates a change in the overall impedance of the high voltage leads and the HV output stage that may effect the utility of the ICD system 10.

Accordingly, the residual voltage (VF) is represented by the equation $$V_F = V_i e^{-T/RC}$$

Where
Vi=the initial charging voltage.
T=time of discharge
R=total resistance=resistance of high voltage leads 16, the output switches 114 & body resistance.
C=Capacitance Accordingly, it is readily understood that if the value of the residual voltage changes significantly from one pulse discharge to the next, that is an indication that the resistance (R) or the capacitance (C) has changed. Since these elements are determined largely by the integrity of the HV output stage 100 and the high voltage leads 16, it is now possible to determine whether those components are operating properly.

In a system in accordance with the present invention, a low voltage (10–20 V) synchronous pacing pulse is provided to the individual's heart through the HV output stage 100 from the high voltage capacitors 108, 110 during diagnostic testing following external defibrillation therapy.

Thereafter, the residual voltage measured on the HV output stage 1 00 is compared to a previously measured residual voltage value, the previously measured value providing an indication that the HV output stage 100 and high voltage leads 16 are operating properly. If there has been a significant change in the residual voltage value, indicating a significant change in the resistance or capacitance, a diagnostic signal may be transmitted with telemetered data indicating the need for a replacement procedure.

Therefore, in a system in accordance with the present invention, the hardware of the existing defibrillation system does not have to be modified. The only change that is necessary is in the level of programmability by the microprocessor 101 to the regulator 102 to accommodate a lower level of charging voltage to be sent through the HV output stage 100 and the provision of the test procedure.

Figure 3:
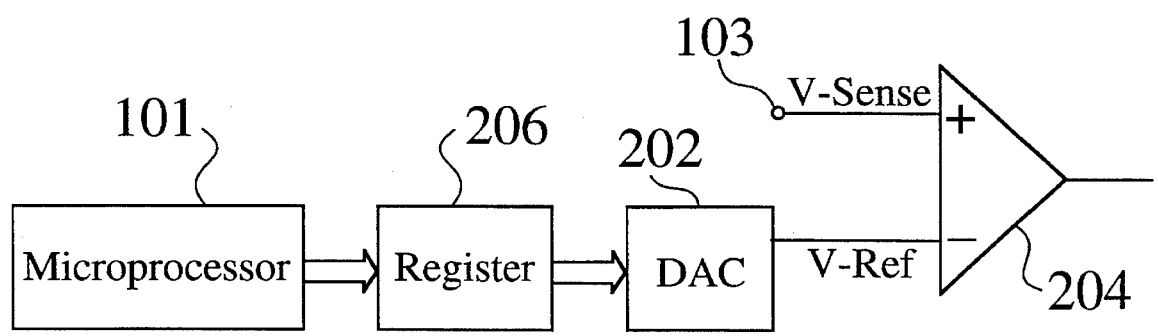
FIG. 3 is a preferred embodiment of a regulator utilized in the ICD of FIG. 2.

Referring now to FIG. 3, what is shown is a block diagram of a preferred embodiment of an system for providing the new level of programmability to the regulator 102. The regulator 102, in this embodiment, comprises a digital to analog (D/A) converter 202 which provides a reference voltage ($V_{REF}$) to a first input of a comparator 204 and receives a digital input signal from a register 206 which is under control of the microprocessor 101. The comparator 204 also receives a voltage sense signal at a second input from a node 103 between a pair of resistors which act as a voltage divider at the output of regulator 102 as seen in FIG. 2.

The sense signal is then compared to $V_{REF}$ received from D/A converter 202. The value of $V_{REF}$ is adjusted by the microprocessor 101 writing the appropriate value to the register 206. Accordingly, the regulator 102 is adjusted to the appropriate voltage level to provide a charging voltage, for example 10–20 volts, rather than the 50–700 volts required for cardioversion or defibrillation therapy. It will be understood that a lower or higher voltage could be used for this charging voltage but that a voltage in this range is preferable from a measurement standpoint.

Figure 4:
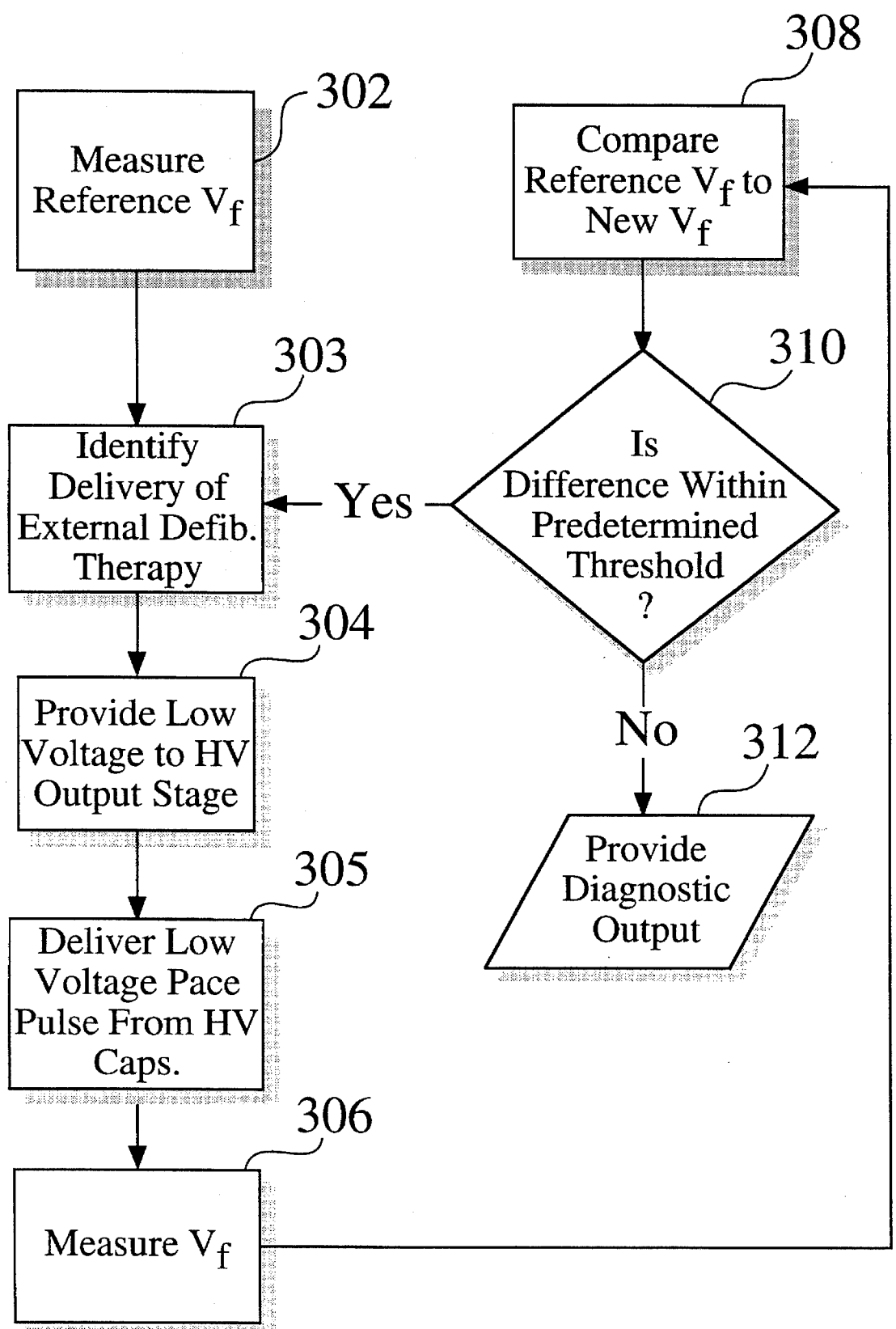
FIG. 4 is a flow chart of the operation of HV output stage in accordance with the present invention.

Referring now to FIG. 4 what is shown is a flow chart which shows the operation of this system for testing high voltage lead integrity and the integrity of the HV output stage in accordance with the present invention.

In this system, the residual voltage of a synchronous pacing pulse from the HV output stage is measured following implantation of the ICD system in the patient utilizing a low voltage between 10–20 volts, via step 302 to provide a reference voltage. This step should be periodically repeated to account for changing electrode resistance values over time caused by the build-up of scar tissue, fibrosis, shifting lead position and other reasons. This initial residual voltage measurement is utilized to provide an indication of the relative change in resistance or capacitance that has occurred in the HV output stage 100 and high voltage leads 16.

Following delivery of external defibrillation therapy step 303, a low voltage (10–20 volts) charge of the same value as the initial low voltage is provided to the high voltage capacitors via step 304 and then synchronously discharged for a predetermined time by the ICD control system via step 305. Thereafter, a new residual voltage is measured, which is essentially the remaining charge of the capacitors via step 306. This new residual voltage is compared with the initial reference residual voltage measurement, via step 308.

Next it must be determined if the difference between the initial reference residual voltage measurement and the next residual voltage measurement is within a predetermined threshold, via step 310. If the difference is within the threshold then return to step 303. However, if the difference is not within the predetermined threshold then there is a problem with the high voltage leads 16 and/or the HV output stage 100. In such an instance an alarm signal could be generated and provided in diagnostic data indicating that the HV output stage 100 and/or high voltage leads should be replaced. For example a change in value of greater than about 30% is an indication that the output stage and/or high voltage leads must be replaced. Accordingly, through this system relative gains or losses in the residual voltage indicate a change in the HV output stage 100 and/or high voltage leads 16.

The procedure shown in FIG. 4 can be utilized after an external defibrillation shock to assess the integrity of the output voltage stage 100. It can also be utilized, for example, to assess the high voltage leads at regular follow up intervals.

Accordingly, through the use of a low voltage synchronous pacing pulse (approximately 10–20 volts) from the high voltage capacitors through the output stage and the subsequent measurement of the residual voltage remaining on the high voltage capacitors after the pulse is terminated, the integrity of the HV output stage 100 and high voltage leads 16 of an ICD system can be readily determined. This testing can take place through no change to the hardware and minimal modification to the software of the ICD system.

While the particular description above contains many specifics, the scope of the invention should not be limited to these details.

Accordingly, although the present invention has been described in accordance with the embodiments shown, one of ordinary skill in the art will recognize that there could be variations to the embodiment and those variations would be within the spirit and scope of the present invention. Accordingly, many modifications may be made by one of ordinary skill without departing from the spirit and scope of the present invention, the scope of which is defined by the following claims.

What is claimed:

1. A method for determining the integrity of a high voltage output stage and high voltage leads of an implantable cardioverter/defibrillator, the output voltage stage including one or more high voltage capacitors, the method comprising the steps of:

(a) charging the one or more high voltage capacitors to a predetermined voltage less than about 50 volts;

(b) discharging the one or more high voltage capacitors for a predetermined time period through the high voltage leads;

(c) measuring a residual voltage on the one or more high voltage capacitors; and (d) comparing the residual voltage to a reference voltage to assess the integrity of the high voltage output stage and high voltage leads.

2. The method of claim 1 wherein step (a) comprises changing the one or more high voltage capacitors to a voltage between about 10 and 20 volts.

3. The method of claim 2 in which the comparing step (d) further comprises the step of (d2) replacing the output voltage stage if the difference is not within the predetermined adjustable range.

4. The method of claim 2 in which the comparing step (d) further comprises the step of (d3) replacing the high voltage leads if the difference is not within the predetermined adjustable range.

5. The method of claim 1 in which the comparing step (d) further comprises the step of:

(d1) determining if a difference between the reference voltage and the residual voltage is within a predetermined adjustable range.

6. A system for determining the integrity of a high voltage output stage and high voltage leads of an implantable cardioverter/defibrillator, the HV output stage including one or more high voltage capacitors, the system comprising:

means for charging the one or more high voltage capacitors to a predetermined voltage less than about 50 volts;

means responsive to the charging means for discharging the one or more high voltage capacitors for a predetermined time period;

means responsive to the discharging means for measuring a residual voltage on the one or more high voltage capacitors; and means responsive to the measuring means for comparing the residual voltage to a reference voltage to assess the integrity of the high voltage output stage and high voltage leads.

7. The system of claim 6 in which the comparing means further comprises means for determining if a difference between the reference voltage and the residual voltage is within a predetermined adjustable range.

8. The system of claim 7 in which the comparing means further comprises the means responsive to the determining means for generating an alarm signal if the difference is not within the predetermined adjustable threshold.

\* \* \* \* \*